US00PP29379P2

(12) United States Plant Patent
Trees

(10) Patent No.: US PP29,379 P2
(45) Date of Patent: Jun. 12, 2018

(54) ***ERYSIMUM* PLANT NAMED 'BALCHERISSAM'**

(50) Latin Name: *Erysimum linifolium*
Varietal Denomination: Balcherissam

(71) Applicant: Ball Horticultural Company, West Chicago, IL (US)

(72) Inventor: Scott C. Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days. days.

(21) Appl. No.: 15/731,475

(22) Filed: Jun. 14, 2017

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Annette H Para
(74) *Attorney, Agent, or Firm* — Audrey Charles

(57) ABSTRACT

A new and distinct cultivar of *Erysimum* plant named 'Balcherissam', characterized by its medium yellow-orange and lavender colored flowers, dark green-colored foliage, and moderately vigorous, mounded-upright growth habit, is disclosed.

1 Drawing Sheet

Latin name of genus and species of plant claimed: *Erysimum linifolium.*

Variety denomination: 'Balcherissam'.

BACKGROUND OF THE INVENTION

The present invention relates to a new and distinct cultivar of *Erysimum* plant botanically known as *Erysimum linifolium* and hereinafter referred to by the cultivar name 'Balcherissam'.

The new cultivar originated in a controlled breeding program in Guadalupe, Calif. during October 2013. The objective of the breeding program was the development of *Erysimum* cultivars that flower without vernalization and continue to flower through summer heat conditions.

The new *Erysimum* cultivar is the result of open-pollination. The female (seed) parent of the new cultivar is the proprietary *Erysimum linifolium* breeding selection coded 'ERY-200', not patented, characterized by its light yellow and lavender-colored flowers, dark grey-green colored foliage, and vigorous, semi-upright growth habit. The male (pollen) parent of the new cultivar is unknown. The new cultivar was discovered and selected as a single flowering plant within the progeny of the above stated open-pollination during July 2014 in a controlled environment in Guadalupe, Calif.

Asexual reproduction of the new cultivar by terminal stem cuttings since July 2014 in Guadalupe, Calif. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balcherissam' as a new and distinct cultivar of *Erysimum* plant:

1. Medium yellow-orange and lavender colored flowers;
2. Dark green-colored foliage; and
3. Moderately vigorous, mounded-upright growth habit.

Plants of the new cultivar differ from plants of the female parent primarily in having and extended flowering season and a more mounded growth habit.

Of the many commercially available *Erysimum* cultivars, the most similar in comparison to the new cultivar is Cheers Mighty Mauve 'Balchermauv' U.S. Plant Pat. No. 26,604. However, in side by side comparisons, plants of the new cultivar differ from plants of 'Balchermauv' in at least the following characteristics:

1. Plants of the new cultivar have a flower color different from plants of 'Balchermauv';
2. Plants of the new cultivar have a larger flower diameter than plants of 'Balchermauv'; and
3. Plants of the new cultivar have darker colored foliage than plants of 'Balchermauv'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs differ slightly from the color values cited in the detailed description, which accurately describes the colors of 'Balcherissam'. The plants were grown in one-gallon containers for approximately seven months in a glass-covered greenhouse in Elburn, Ill. Plants were given one pinch before and one pinch after transplant.

DETAILED BOTANICAL DESCRIPTION

Figure 1:
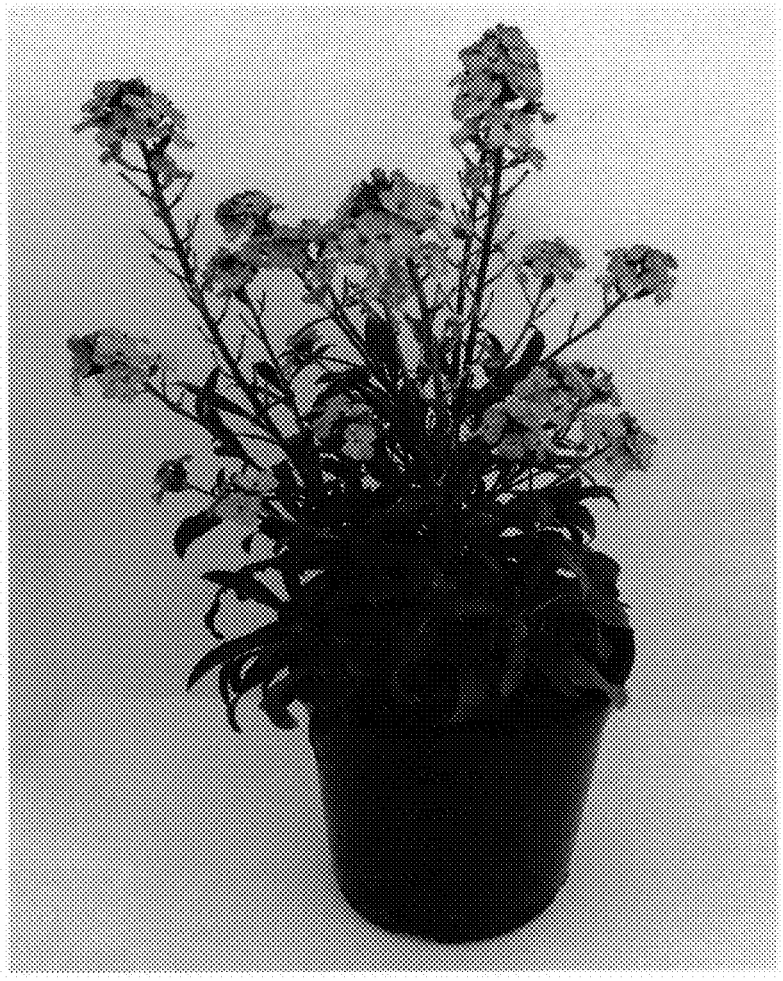
FIG. 1 illustrates a side view of the overall growth and flowering habit of 'Balcherissam'.
Figure 2:
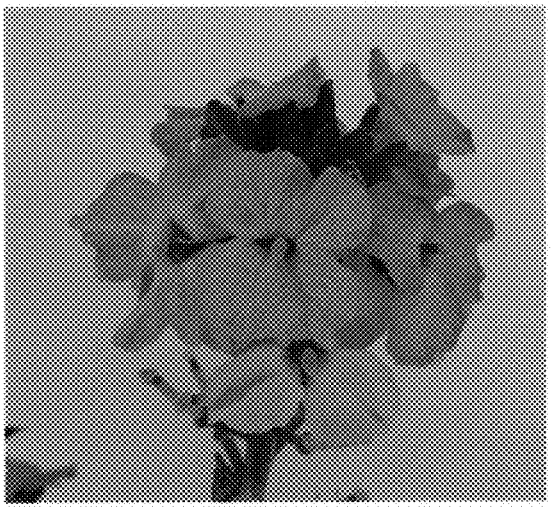
FIG. 2 illustrates a close-up view of an individual inflorescence of 'Balcherissam'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in April 2017 under natural light conditions in West Chicago, Ill.

The following descriptions and measurements describe plants produced from cuttings from stock plants and grown in a glass-covered greenhouse under conditions comparable to those used in commercial practice. The plants were grown utilizing a soilless growth medium in one-gallon containers for approximately seven months in Elburn, Ill. Plants were transplanted in late fall from rooted cuttings and were given one pinch before and one pinch after transplant. Greenhouse temperatures were maintained during the winter months at approximately 45° F. to 65° F. (7.2° C. to 18.3° C.) during the day and approximately 35° F. to 45° F. (1.7° C. to 7.2° C.) during the night. For the final 12 weeks, greenhouse temperatures were maintained at approximately 65° F. to 70° F. (18.3° C. to 21.1° C.) during the day and approximately 55° F. to 60° F. (12.8° C. to 15.6° C.) during the night. No supplemental lighting was provided. Measurements and numerical values represent averages of typical plants.

Botanical classification: *Erysimum linifolium* cultivar Balcherissam.

Parentage:

*Female parent.*—Proprietary *Erysimum linifolium* breeding selection coded 'ERY-200', not patented.

*Male parent.*—Unknown.

Propagation:

*Type cutting.*—Terminal stem.

*Time to initiate roots.*—Approximately 10 to 12 days.

*Time to produce a rooted cutting.*—Approximately 42 to 49 days.

*Root description.*—Fine, fibrous.

*Rooting habit.*—Freely branching.

Plant description:

*Commercial crop time.*—Approximately 10 to 12 weeks from a rooted cutting to finish in a 15 cm pot.

*Growth habit and general appearance.*—Perennial, moderately vigorous, mounded-upright growth habit.

*Hardiness.*—USDA Zone 7a (0° F. to 5° F./−17.8° C. to −15° C.).

*Size.*—Height from soil level to top of plant plane: Approximately 38.0 cm. Width: Approximately 30.0 cm.

*Branching habit.*—Pinching improves basal branching. Quantity of main branches per plant: Approximately 10.

*Branch.*—Shape: Ribbed. Strength: Strong. Length to base of inflorescence: Approximately 13.0 cm. Diameter: Approximately 4.0 mm. Length of central internode: Approximately 2.0 mm. Texture: Densely pubescent with appressed hairs. Color of young and mature stems: Closest to 146B.

Foliage description:

*General description.*—Quantity of leaves per main branch: Approximately 7. Fragrance: None detected. Form: Simple. Arrangement: Alternate in a spiral.

*Leaves.*—Aspect: Perpendicular or acute angle to stem, tip downward turning with age. Shape: Oblanceolate. Margin: Dentate to entire, slightly undulate. Apex: Acute. Base: Attenuate, sessile. Venation pattern: Pinnate. Length of mature leaf: Approximately 11.5 cm. Width of mature leaf: Approximately 1.5 cm. Texture of upper and lower surfaces: Densely pubescent with appressed hairs. Color of upper surface of young and mature foliage: Closest to, but darker than 137A with midvein of 146D, other venation indistinguishable. Color of lower surface of young and mature foliage: Closest to 137B with midvein of 146C, other venation indistinguishable.

Flowering description:

*Flowering habit.*—'Balcherissam' is freely flowering under outdoor growing conditions with substantially continuous blooming from early spring through autumn.

*Lastingness of individual flower on the plant.*—Approximately 6 to 8 days.

Inflorescence description:

*General description.*—Type: Terminal raceme. Quantity per plant: Approximately 15. Fragrance: Slight, sweet. Length or height: Approximately 16.0 cm. Width: Approximately 5.0 cm. Quantity of fully open flowers per inflorescence: Approximately 10.

Flower description:

*Type.*—Solitary, self-cleaning.

*Bud.*—Rate of opening: Generally takes 4 to 5 days for bud to progress from first color to fully open flower.

*Bud just before opening.*—Shape: Ovoid and slightly flattened. Length: Approximately 1.0 cm. Diameter: Approximately 5.0 mm. Color: Calyx of 137B with base of 145B; petals of 1A.

*Corolla.*—Shape: Lobes cruciform with claws surrounded by calyx. Aspect: Facing upward and outward. Diameter: Approximately 2.2 cm. Depth: Approximately 1.8 cm.

*Petals.*—Quantity: 4. Shape: Obovate. Margin: Entire, undulate. Apex: Obtuse. Base: Attenuate. Length of lobes: Approximately 1.0 cm. Width of lobes: Approximately 1.2 cm. Length of claws: Approximately 1.0 cm. Width of claws at widest point: Approximately 2.0 mm. Texture of upper and lower surfaces: Glabrous. Color of upper surface of lobes when first open: 163C with an overlay of 173C. Color of lower surface of lobes when first open: 163D with an overlay of 173D. Color of upper surface of lobes when fully open: 173C overlay fades as petals transition to N82D with venation of N82C. Color of lower surface of lobes when fully open: 173D overlay fades as petals mature to N82D. Color of upper and lower surfaces of claws: NN155A with a midvein of 145A.

*Calyx.*—Shape: Tubular. Diameter: Approximately 5.0 mm.

*Sepals.*—Quantity per flower: 4, distinct. Shape: Lanceolate. Apex: Acute. Base: Truncate. Length: Approximately 1.0 cm. Width: Approximately 3.0 mm. Texture of inner surface: Glabrous. Texture of outer surface: Moderately pubescent with appressed hairs. Color of inner surface: 137A with base of 145A. Color of outer surface: 137B with base of 145B.

*Pedicel.*—Strength: Strong. Aspect: Acute angle to stem. Length: Approximately 4.0 mm. Diameter:

Approximately 1.5 mm. Texture: Densely pubescent with appressed hairs. Color: 137C.

*Reproductive organs.*—Androecium: Stamen quantity: 6 per flower. Stamen length: Approximately 9.0 mm, 1 pair slightly shorter and inserted lower. Filament texture: Glabrous. Filament color: 145D. Anther shape: Sagittate, dorsifixed. Anther length: Approximately 2.0 mm. Anther color: 4D. Pollen amount: None observed. Gynoecium: Pistil quantity: 1 per flower. Pistil length: Approximately 1.2 cm. Stigma shape: Bifid. Stigma length: Approximately 1.0 mm. Stigma color: 151D. Style length: Approximately 1.0 mm. Style color: 144A. Ovary length: Approximately 1.0 cm. Ovary width: Approximately 1.5 mm. Ovary texture: Densely pubescent with appressed hairs. Ovary color: 144A, appears lighter colored due to pubescence.

Seed and fruit production: Neither seed nor fruit production has been observed.

Disease and pest resistance: Resistance to pathogens and pests common to *Erysimum* has not been observed.

What is claimed is:

1. A new and distinct cultivar of *Erysimum* plant named 'Balcherissam', substantially as herein illustrated and described.

* * * * *